US008690885B2

(12) United States Patent
Smith

(10) Patent No.: US 8,690,885 B2
(45) Date of Patent: Apr. 8, 2014

(54) SURGICAL AIMING DEVICE

(75) Inventor: Graham Smith, Newburyport, MA (US)

(73) Assignee: Smith & Nephew, Inc., Memphis, TN (US)

( * ) Notice: Subject to any disclaimer, the term of this patent is extended or adjusted under 35 U.S.C. 154(b) by 128 days.

(21) Appl. No.: 13/016,081

(22) Filed: Jan. 28, 2011

(65) Prior Publication Data

US 2012/0197259 A1 Aug. 2, 2012

(51) Int. Cl.
*A61B 17/17* (2006.01)

(52) U.S. Cl.
USPC .......................................... 606/96

(58) Field of Classification Search
USPC ............... 606/86 R–88, 96–98, 104; 433/73; 33/286, 511, 512, 645
See application file for complete search history.

(56) References Cited

U.S. PATENT DOCUMENTS

| | | | |
|---|---|---|---|
| 4,722,331 A | 2/1988 | Fox | |
| 4,739,751 A | 4/1988 | Sapega et al. | |
| 5,176,515 A * | 1/1993 | Andrews | 433/24 |
| 5,514,144 A | 5/1996 | Bolton | |
| 5,643,273 A | 7/1997 | Clark | |
| 5,688,284 A | 11/1997 | Chervitz et al. | |
| 5,968,050 A | 10/1999 | Torrie | |
| 6,120,511 A * | 9/2000 | Chan | 606/96 |
| 6,187,011 B1 * | 2/2001 | Torrie | 606/96 |
| 7,192,431 B2 * | 3/2007 | Hangody et al. | 606/87 |
| 2008/0306487 A1 | 12/2008 | Hart | |
| 2009/0163766 A1 | 6/2009 | Torrie et al. | |

FOREIGN PATENT DOCUMENTS

| | | |
|---|---|---|
| EP | 1917921 A2 | 5/2008 |
| FR | 2901465 | 11/2007 |
| FR | 2911264 A1 | 7/2008 |
| WO | WO99/29237 | 6/1999 |

OTHER PUBLICATIONS

International searchreport and written opinion regarding International patent application PCT/US2012/023055 mailed on Apr. 2, 2012.

* cited by examiner

*Primary Examiner* — Todd Manahan
*Assistant Examiner* — Eric S Gibson
(74) *Attorney, Agent, or Firm* — Chapin IP Law, LLC

(57) ABSTRACT

A hinged pivoting guide for positioning a femoral tunnel in anterior cruciate ligament (ACL) reconstruction locates a drilling hole for placement that optimally penetrates a minimal depth of soft tissue (skin, muscle, etc.) yet directs drilling into a sufficiently rigid and structurally sound area of the femur. The hinged guide allows placement of an aimer point at a desired drilling exit location on the femur. The hinge is adapted to secure the aimer at a degree of rotation about an axis defined by the hinge rotation, such that the axis passes through the aimer point throughout rotation of the hinge while maintaining the aimer point in line with an insertion guide slideably movable through the aperture in the handle, the aperture defined by an insertion axis extending toward the aimer point such that the aimer point remains disposed at the intersection of the hinge axis and the insertion axis.

25 Claims, 9 Drawing Sheets

SURGICAL AIMING DEVICE

BACKGROUND

Reconstructive bone and ligament surgery often involves drilling into skeletal members to attach connective elements such as ligament and tendon grafts, as well as various artificial replacements and/or attachments for articulated joints. In particular, reconstructive surgery involving the anterior cruciate ligament (ACL) is becoming particularly significant because the effectiveness of reconstruction can have a profound effect on the subsequent athletic ability of the patient. For professional athletes, for example, an effective ACL repair can salvage an otherwise career ending injury. Similarly, an improperly treated ACL injury can be a permanent detriment even to an amateur athlete.

SUMMARY

Reconstructive surgery involving functional, structural fixation to bone members often involves drilling into a structurally sound area of the corresponding bone. In an ACL repair, antegrade drilling of the femur is becoming more common. A damaged ACL is often replaced with a graft from a patellar tendon or a semitendinosus tendon. Such a repair is facilitated by tunnels formed in the tibia and femur for use in implanting the graft in the patient's knee. Recent studies suggest more accurate placement is achievable by such antegrade femoral drilling than by conventional approaches such as drilling the femoral tunnel through the tibial tunnel. The graft may then be secured in the tunnels by fixation means, such as, for example, interference screws or sutures tied to screw posts. The femur, in particular, is often subjected to more substantial forces because it often bears the entire weight of the patient, and being the largest human bone, may be relied upon to accommodate a substantial connective force from a surgically added structure.

Configurations herein are based, in part, on the observation that conventional arrangements for surgical or arthroscopic drilling rely on a fixed aimer that may impede positioning of the handle and insertion guide for optimal positioning of a drill hole at an insertion point. An optimal placement defines a point of entry for a drilling hole that displaces minimal soft tissue depth while engaging a rigid structure (such as a knee bone) at a structurally sound location. Conventional approaches using such a fixed, rigid aimer hinder the ability to achieve optimal interarticular tunnel placement.

In ACL reconstruction involving such drilling, therefore, attachment of structural surgical tethers, such as grafts and artificial connectors, should be performed at a structurally sound location on the femur. Configurations herein disclose a drilling guide adapted for positioning a drilling tunnel in (ACL) reconstruction. Typically, a drilling guide adapted for insertion into a joint region locates a drilling exit point, while a surgeon manipulates the handle of the drilling guide to locate an entry location. Unfortunately, conventional arrangements suffer from the shortcoming that drilling guides for directing placement of the drilled hole are universal, in that a single straight design having a fixed relation of an aimer arm and a handle identify a point of drilling. Conventional approaches, therefore, do not distinguish a left from right knee, nor individual differences in the bone configuration of an individual patient, which compromises the ability to manipulate the drilling guide to pivot around the aimer arm for locating an optimal entry point for drilling. Conventional mechanisms employ a fixed aimer incapable of rotational or pivoting movement around a hinge connection to the arm denoting the drilling exit point. Such arrangements may attempt a similar range of application by employing fixed left and right guides, or a series of fixed angle guides for both right and left application, however this would result in a trial and error administration as well as requiring manufacturing of a range of multiple fixed angle guides.

Configurations herein substantially overcome the above described shortcomings by employing a hinged pivoting guide for positioning a femoral or tibial tunnel, for example, in anterior cruciate ligament (ACL) reconstruction. Locating the drilling hole for placement of the tunnel optimally penetrates a minimal depth of soft tissue (skin, muscle, etc.) yet directs drilling into a sufficiently rigid and structurally sound area of the femur. The hinged guide allows placement of an aimer point at a desired drilling exit location on the femur. The handle includes an aperture indicative of the drilling location, and a surgeon may manipulate the handle by pivoting around the hinge to dispose the aperture at an optimal location while maintaining the same exit location defined by the aimer point. In this manner, an optimal drilling location is selectable by positioning the handle to an area of minimal soft tissue depth and in line with a structurally sound path through the femur.

In further detail, the surgical aiming device as disclosed herein includes a handle coupled to a proximate end of an elongated arm, in which the elongated arm further has a distal end, and a hinge securing an aimer to the distal end for rotational communication around a hinge axis. The aimer has an elongated aimer tip and an aimer point, such that the aimer point is at a distal end of the aimer tip from the hinge, and the aimer tip couples to the arm via the hinge at a proximate end. The hinge is adapted to secure the aimer at a degree of rotation about an axis defined by the hinge rotation, such that the axis passes through the aimer point throughout rotation of the hinge while maintaining the aimer point in line with an insertion guide slideably movable through the aperture in the handle, in which the aperture defines an insertion axis extending toward the aimer point such that the aimer point remains disposed at the intersection of the hinge axis and the insertion axis.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Disclosed below is an example configuration and deployment of the surgical aimer arm. In an example arrangement, an ACL repair employing the surgical aiming device for femoral drilling is shown. Alternate configurations may employ placement on other skeletal structures, or on softer tissue surfaces, and may or may not employ a drilling approach for excavating the insertion tunnel for a guidewire.

Figure 1:
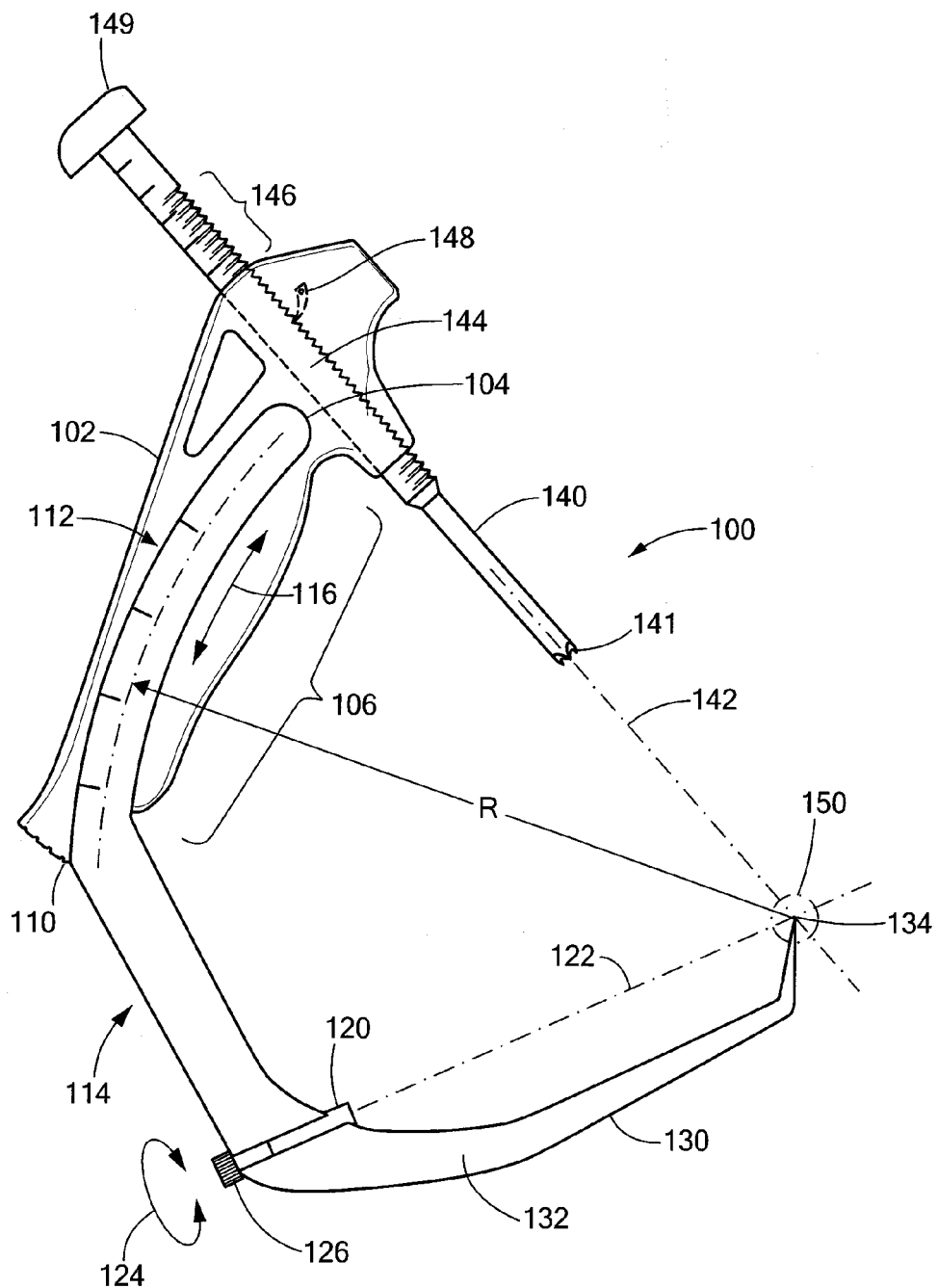
FIG. 1 shows a side view of the surgical aiming device as disclosed herein.

FIG. 1 shows a side view of the surgical aiming device 100 including a handle 102 having a slot 104 defining an arc 106. The handle 102 is shaped for a secure grasp by a surgeon or other operator. An arm 110 has an arced section 112 and a straight section 114. The arced section 112 is shaped to slideably engage with the slot 104 in the handle 102 for movement according to arrow 116. The straight section 114 has a hinge 120 for securing an aimer 130 to the straight section 114 at the opposed end distal from the arced section 112. The hinge 120 adapts the aimer 130 for rotational communication with the straight section 114 around a hinge axis 122, as shown by arrow 124. The hinge 120 secures the aimer 130 via a screw 126 or other suitable pivotal coupling around the hinge axis 122.

The aimer 130 includes an elongated aimer tip 132 extending from the hinge and an aimer point 134 at a distal end of the aimer tip 132 from the hinge 120. The aimer tip 132 couples to the straight section 114 via the hinge 120 at a proximate end. The handle 102 further includes an insertion guide 140 adapted for slideable movement within an aperture 144 in the handle 102 along an insertion axis 142. The insertion guide 140 has slanting teeth 146 for selective ratcheting engagement with a pawl 148 when the insertion guide 140 is rotated via an insertion knob 149 such that the teeth 146 engage the pawl 148. The insertion axis 142 passes through the aimer point 134 at an intersection 150 of the hinge axis 122, thus the aimer tip 132 extends such that the aimer point 134 is disposed on the insertion axis 142 throughout the range of rotation 124 of the aimer 130.

The arm 110 is adapted for arcuate movement relative to the handle 102 as defined by the arc 106, shown by arrows 116. The aimer point 134 is the center of a circle defining the arc 106 in the handle 102 through which the arced section 112 slideably engages, thus the aimer point 134 retains its position at the intersection 150 during the arcuate movement 116. Further, as the hinge 120 is adapted to secure the aimer 130 at a degree of rotation about an axis 122 defined by the hinge 120 and passing through the aimer point 134, the aimer point remains at the intersection 150 throughout movement of the arm 130 and arced section 112.

The insertion guide 140 has a hollow core (176, FIG. 6 below) for subsequent guidewire access, discussed further below. A taper, serration, or other suitable engaging edge on the tip 141 of the insertion guide facilitates identification of an incision point, and subsequently for engaging a bone or other hard surface for fixing the insertion guide for the guidewire. Typically a soft tissue incision is made where the tip 141 contacts soft tissue, the insertion guide 140 inserted until hard material (i.e. bone) is encountered, and the tip engages the bone facilitated by the ratcheting action to avoid slippage during guidewire insertion.

Figure 2:
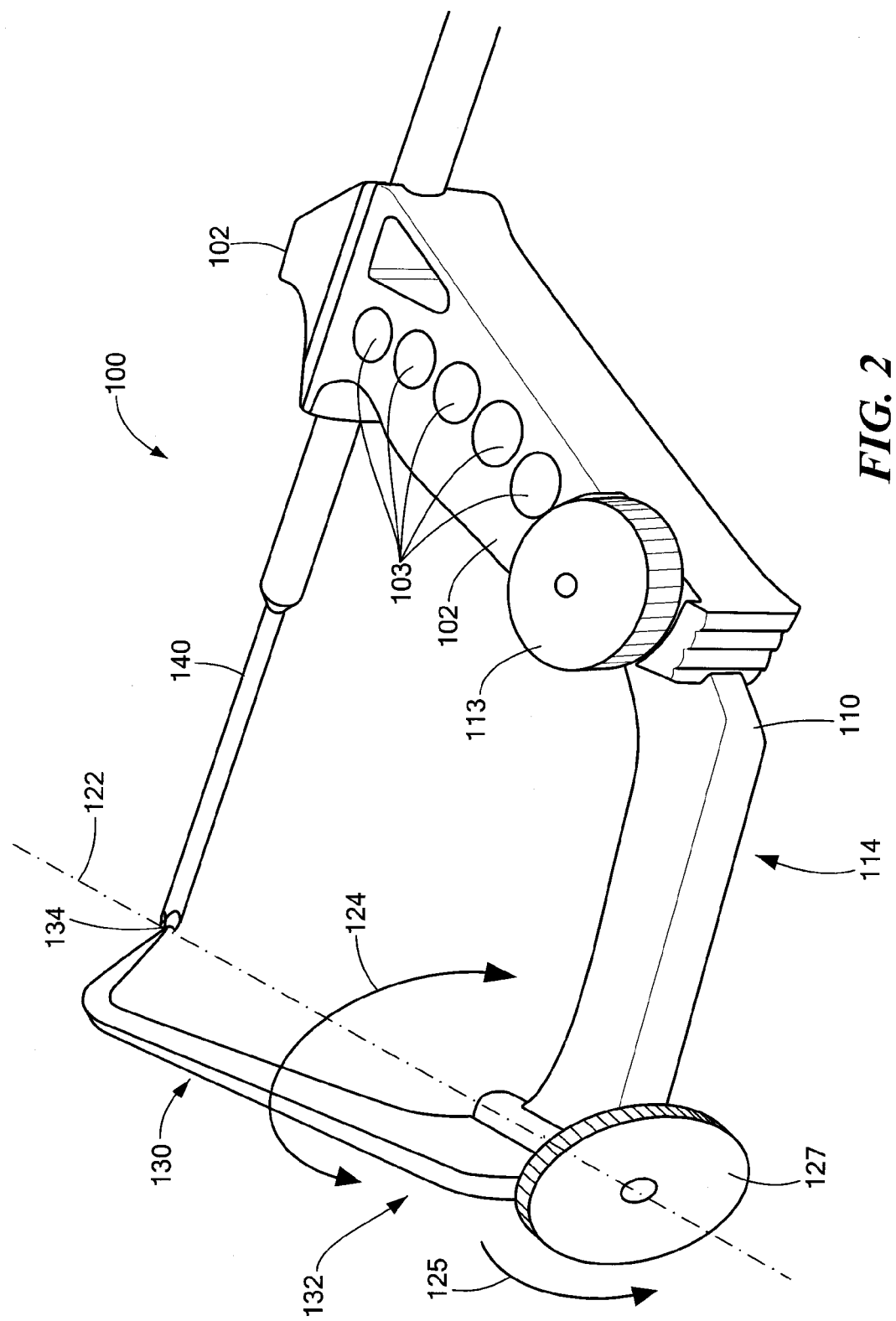
FIG. 2 shows a perspective view of the surgical aiming device of FIG. 1.

FIG. 2 shows a perspective view of the surgical aiming device of FIG. 1. Referring to FIGS. 1 and 2, the handle 102 includes apertures 103 for weight reduction. The insertion guide 140 is extendable to the aimer point 134 to define a drilling and/or insertion hole for a guide wire along the insertion axis 142 through a range from the aperture 144 in the handle to the aimer point 134. A pivot knob 127 rotates the hinge screw 126 (arrow 125) for securing and releasing the hinge 120 at various degrees of rotation (pivot) through a range, shown at a pivot angle 124. The arced section 112 is fixable by fixation knob 113.

Figure 3:
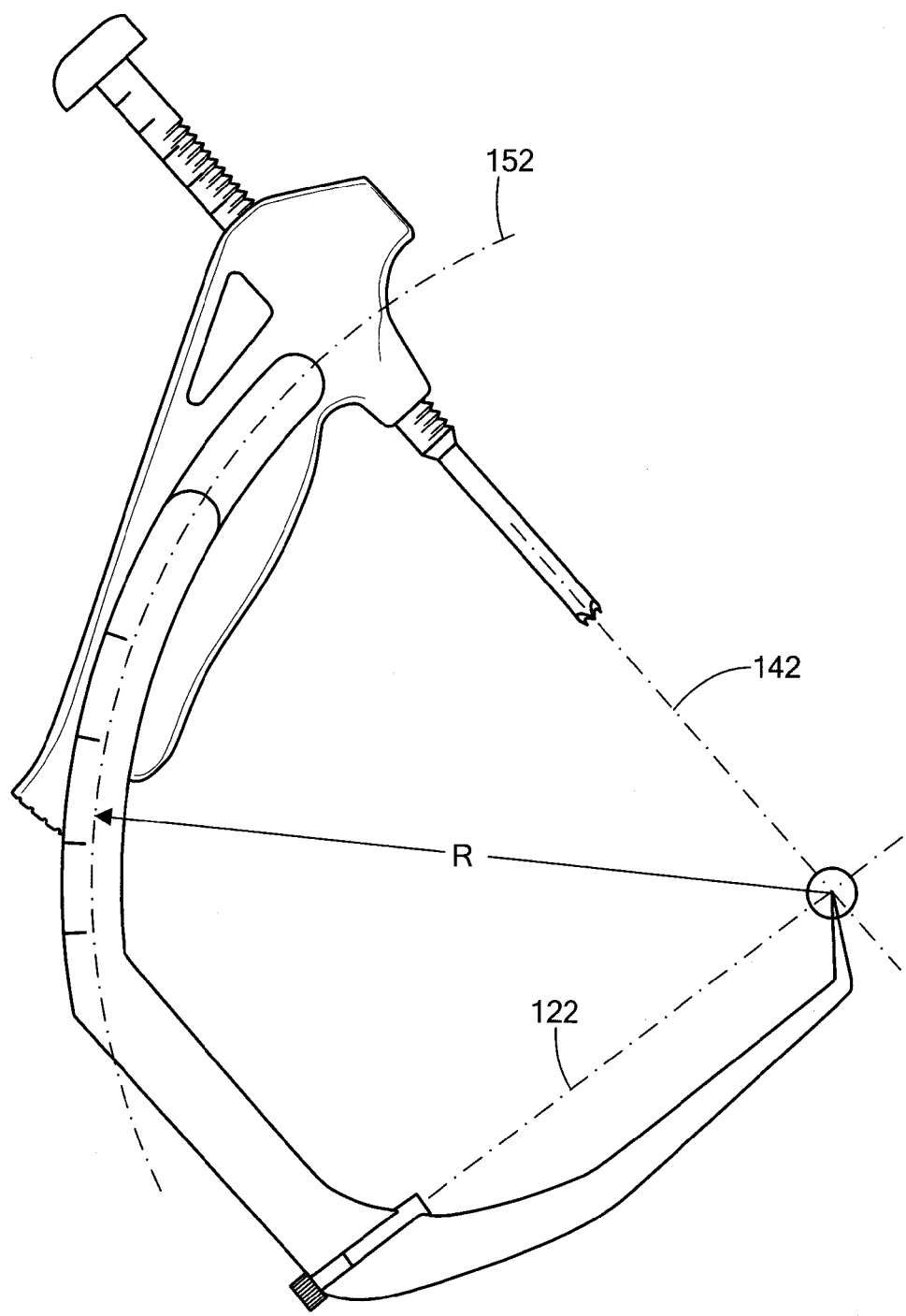
FIG. 3 shows a side view of the surgical aiming device as in FIG. 1 with a partially extended arced section.

FIG. 3 shows a side view of the surgical aiming device as in claim 1 with a partially extended arced section 112. Referring to FIGS. 1 and 3, the arced section 112 is partially extended exposing the apertures 103 in the handle 102. The insertion axis 142 and hinge axis 122 still intersect 150 at the aimer point 134, since the arm 110 travels along an arc 116 on the circle 152 with the aimer point 134 at the center.

Figure 4:
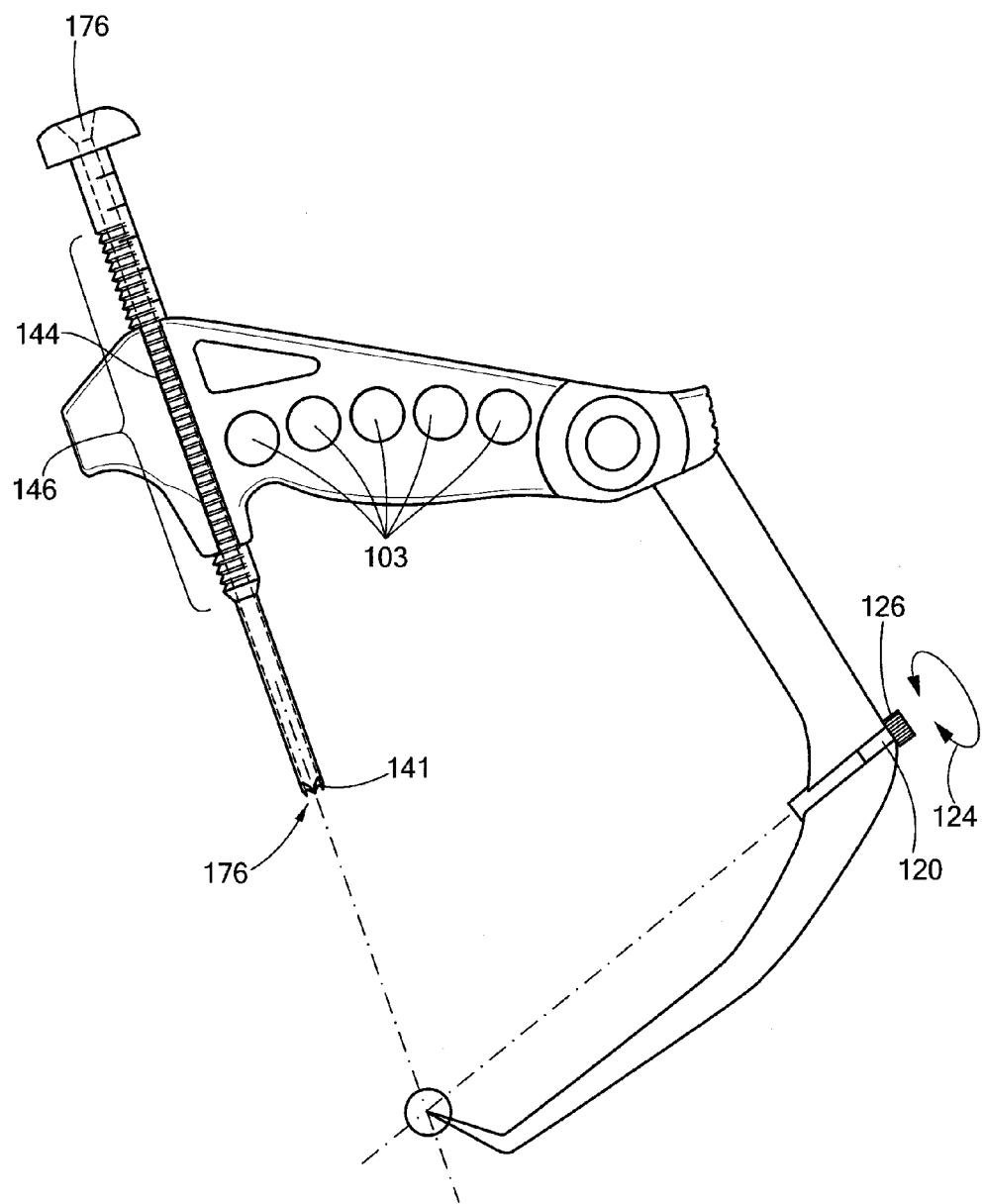
FIG. 4 shows an opposed side view of the surgical aiming device of FIG. 1.

FIG. 4 shows an opposed side view of the surgical aiming device of FIG. 1. Referring to FIGS. 1 and 4, the aperture 144 in the handle is visible showing the slanting teeth 146 providing ratcheting movement to the insertion guide 140. The hollow core 176 of the insertion guide 140 allows passing of a guidewire 154 (FIG. 6, below) through an insertion tunnel 174 formed from rotation of the insertion guide 140 or from a separate drilling device.

Figure 5:
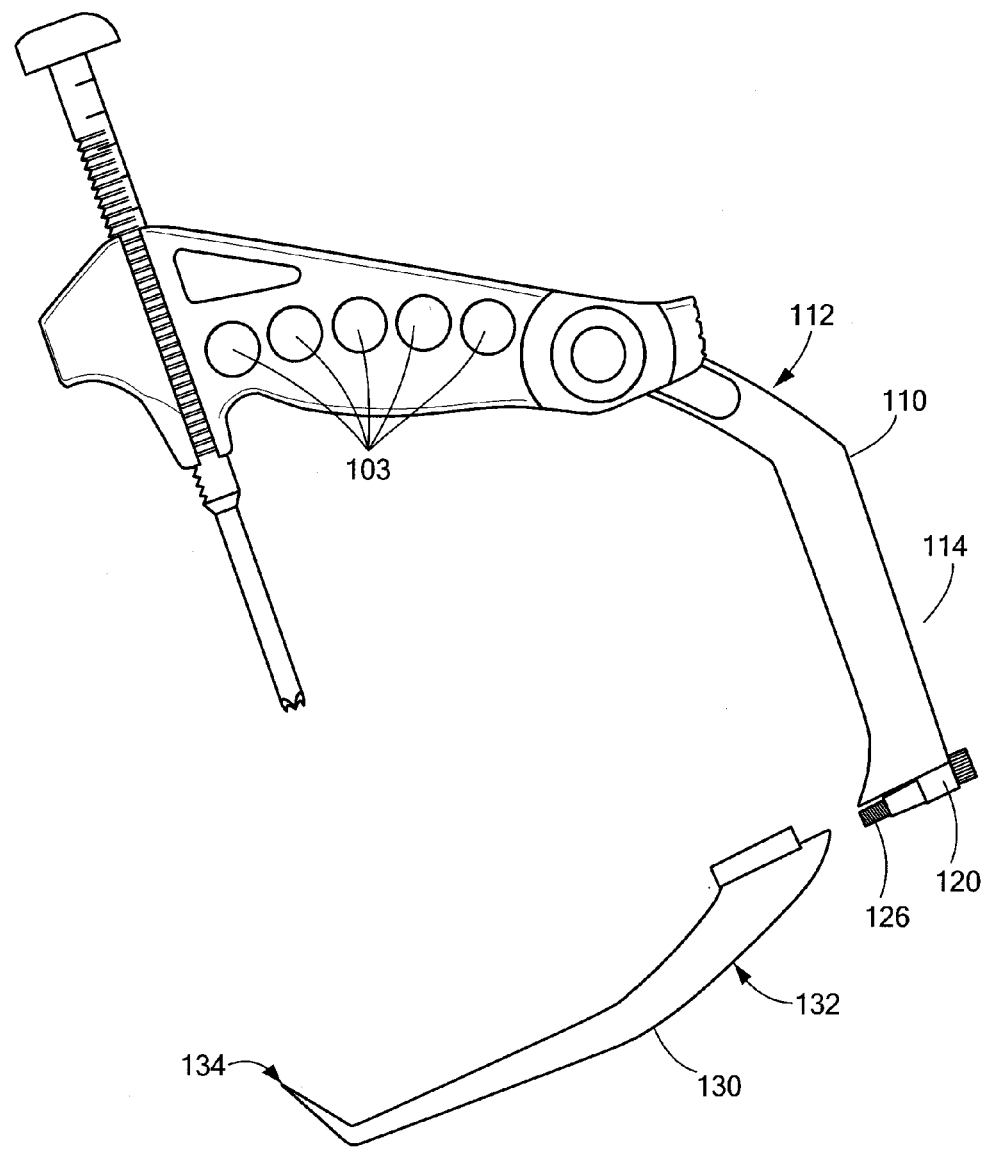
FIG. 5 shows an alternate view of the surgical aiming device of FIG. 4 having a partially extended arced section and disengaged arm.

FIG. 5 shows an alternate view of the surgical aiming device of FIG. 4 having a partially extended arced section 112 and disengaged arm 130. The partial extension of the arced portion 112 of the arm 110 is shown by the apertures 103 only partially obscured by the arced portion 112. The hinge 120 employs the securing screw 126 for securing the arm 130, shown detached with a threaded portion of the securing screw 126 visible.

Figure 6:
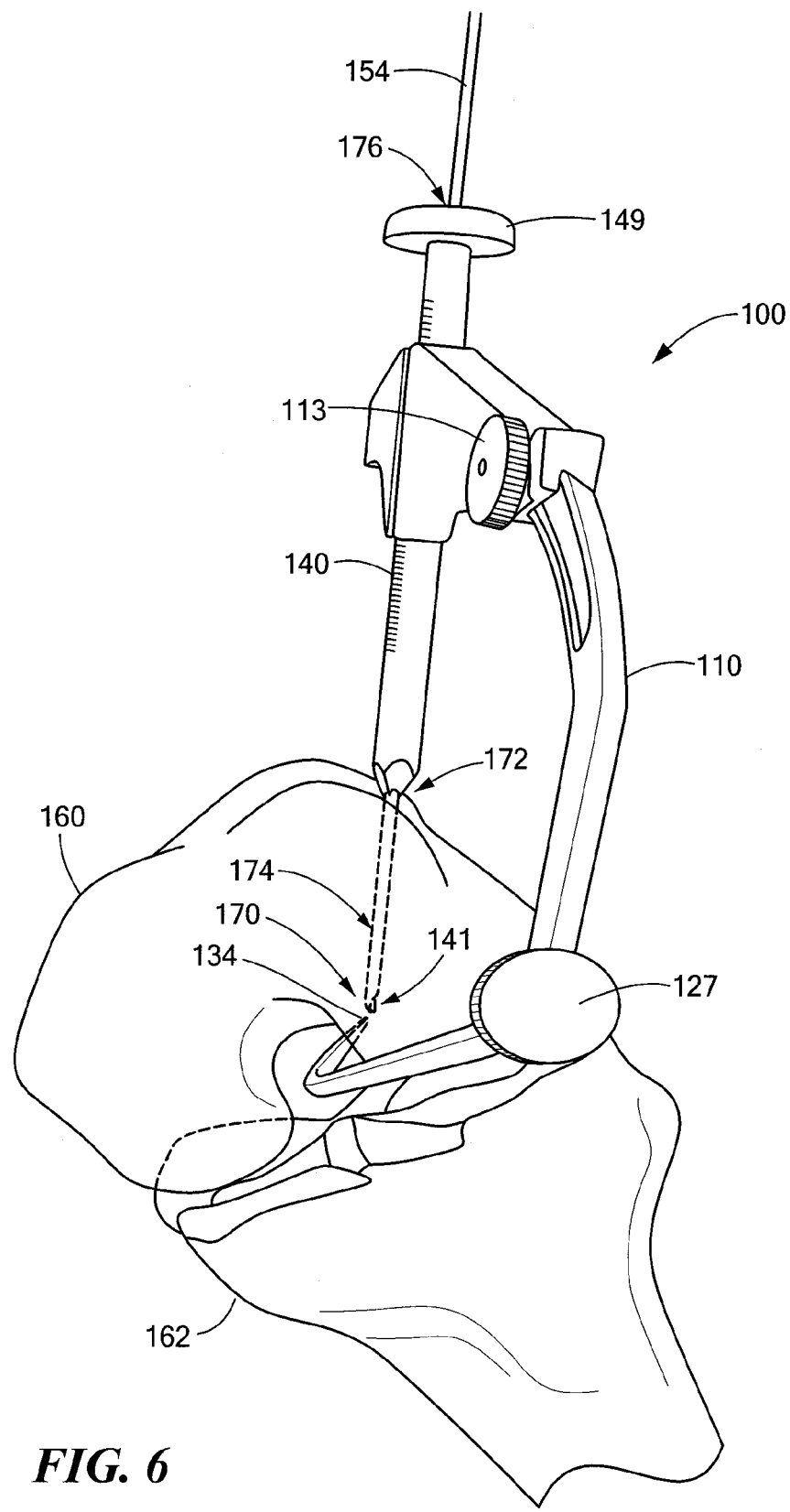
FIG. 6 shows a perspective view of the aimer arm disposed at a surgical site.

FIG. 6 shows a perspective view of the surgical device 100 disposed at a surgical site. As indicated above, ACL repairs often involve surgical drilling through the femur 160 and tibia 162 for passing a guidewire 154 through the insertion guide 140. Referring to FIGS. 1 and 6, an example of using the surgical aiming device 100 for such an application is shown. The surgeon disposes the aimer point 134 at a target location 170 within the surgical site, such as an anatomically sound location on the femur 160. Typically this would be the same location as the prior attachment of the ligament being repaired, but other suitable locations may be marked/aimed. The surgeon frees the securing mechanism of the hinge 120 such as by loosening the hinge knob 127, and disposes the arm 110 and handle 102 to a suitable location for drilling as defined by an incision point and corresponding drilling site 172 (note that the incision point often defines a soft tissue location along the insertion axis for insertion of the insertion guide towards the drilling site 172). A serrated or tapered edge at the tip 141 of the insertion guide 140 passes soft tissue, and contacts the drilling site 172 at the bone, cartilage, or other hard surface. The tip 141 is formed so as to engage the bone surface after penetrating the soft tissue through the insertion, and may be a pyramidal, serration, or tapered edge, for example. A drill may subsequently be employed to further excavate an insertion tunnel 174, formed from the guide wire 154 passing through the hollow core 176 of the insertion guide 140.

Figure 7:
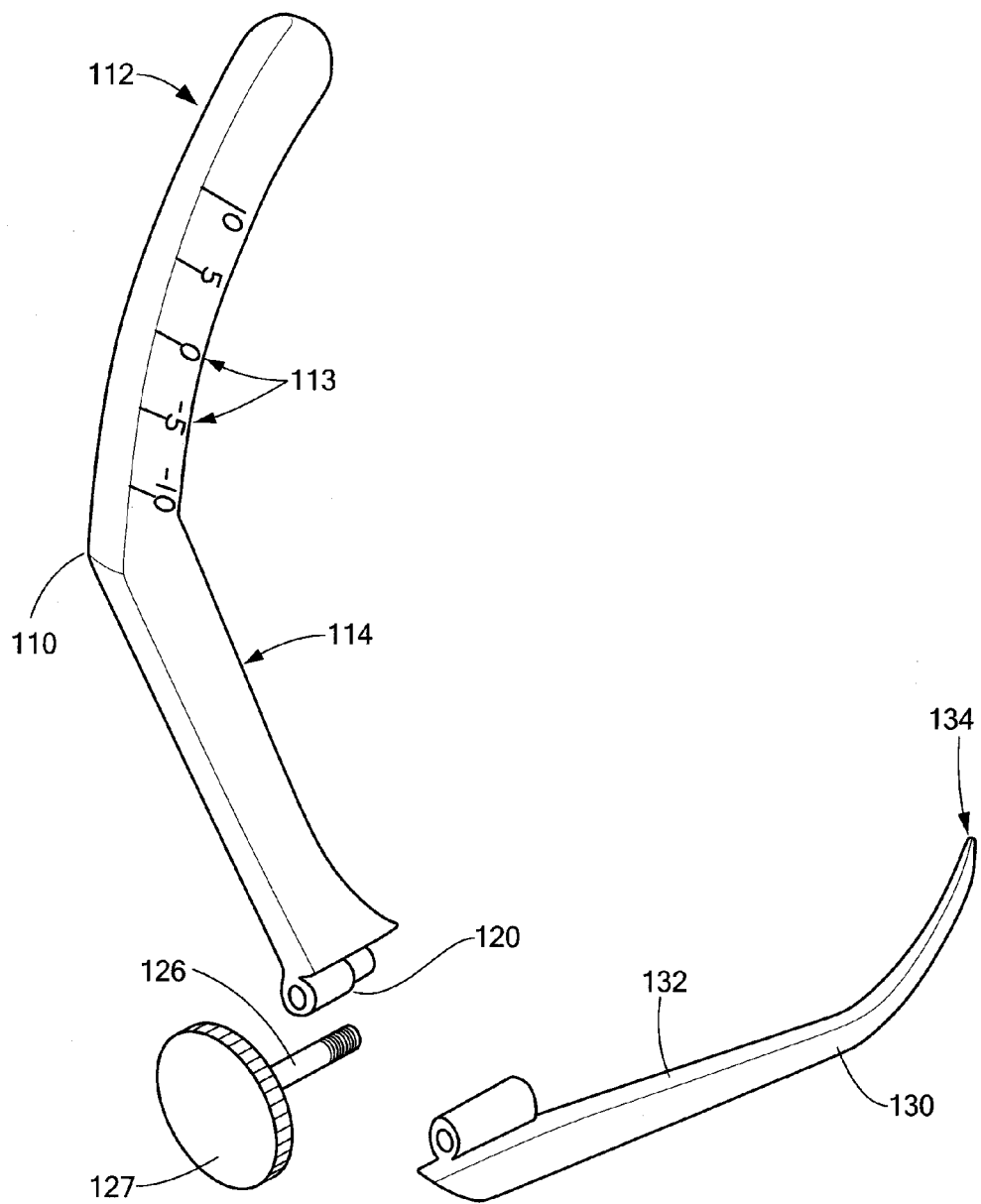
FIG. 7 shows an exploded view of the arm of FIG. 1.

FIG. 7 shows an exploded view of the arm 110 of FIG. 1, showing tick markings 113 metering arcuate extension of the arced portion 112, and the separation of the hinge 120 rotationally securing the straight portion 114 of the arm 110 to the aimer 130.

Figure 8:
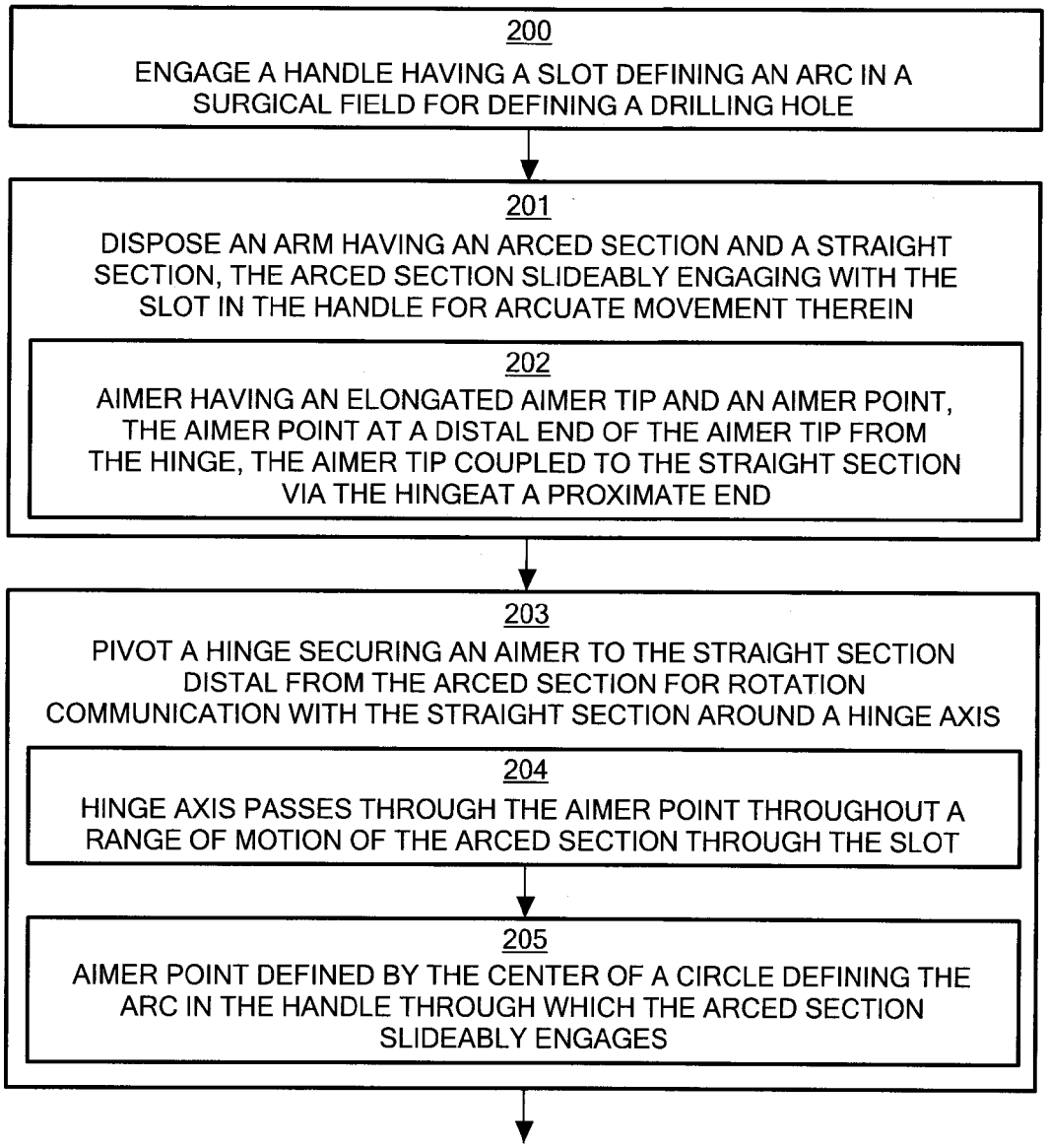
FIGS. 8-9 show a procedural sequence employing the surgical aiming device of FIG. 1.
Figure 9:
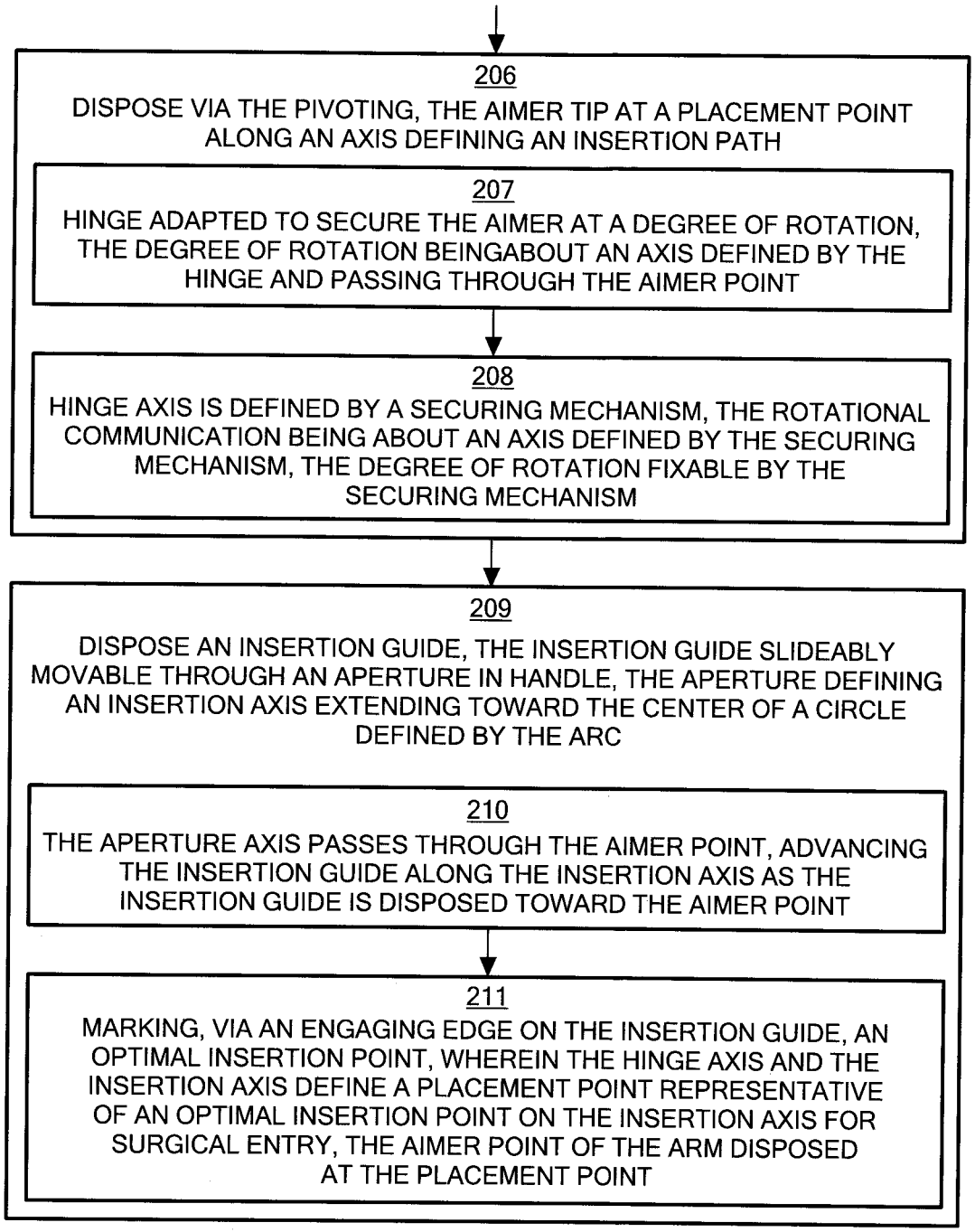

FIGS. 8-9 show a procedural sequence employing the surgical aiming device of FIG. 1. Referring to FIGS. 1 and 8-9, locating an optimal insertion point allows locating the aimer point 134 at a target location, and manipulating the handle 102 via pivoting of the hinge 120 and sliding the arced section 110 to dispose the insertion guide 140 accordingly, as follows.

A method for surgical drilling using the surgical aiming device disclosed herein includes, at step 200 engaging a handle 102 having a slot 104 defining an arc 106 in a surgical field for defining a drilling hole 174 by disposing an arm 110 having an arced section 112 and a straight section 114, such that the arced section 112 slideably engages with the slot 104 in the handle 110 for arcuate movement therein, as depicted at step 201.

The arm 110 hindgedly attaches to the aimer 110 having an elongated aimer tip 132 and an aimer point 134, such that the aimer point 134 is at a distal end of the aimer tip 132 from the hinge 120, and the aimer tip 132 couples to the straight section 114 via the hinge 120 at a proximate end, as disclosed at step 202.

An operator pivots the hinge 120 securing the aimer 130 to the straight section 114 distal from the arced section 112 for rotational communication with the straight section 114 around a hinge axis 122, as shown at step 203. The hinge axis 122 passes through the aimer point 134 throughout a range of motion 116 of the arced section 112 through the slot 104, as depicted at step 204. The aimer point 134 remains defined by the center of a circle 152 defining the arc 106 in the handle through which the arced section 112 slideably engages, as disclosed at step 205. The surgeon or operator disposes, via the pivoting, the aimer tip 134 at a placement point 170 along the axis 142 defining an insertion path, as shown at step 206. The hinge 120 is adapted to secure the aimer 130 at a degree of rotation 124, such that the degree of rotation 124 is about an axis 122 defined by the hinge 120 and passing through the aimer point 134, as depicted at step 207. The hinge axis 122 is defined by a securing mechanism, such that the rotational communication 124 is about the axis 122 defined by the securing mechanism, and the degree of rotation 124 is fixable by the securing mechanism, as shown at step 208. In the example arrangement, the securing mechanism is provided by the securing screw 126 and knob 127, however alternate securement arrangements may be employed.

The operator or surgeon disposes the insertion guide 140, such that the insertion guide 140 is slideably movable through an aperture 144 in the handle 110. The aperture 144 defines an insertion axis 142 extending toward the center of a circle 152 defined by the arc 106, as disclosed at step 209. This includes, at step 210, wherein the aperture 144 axis passes through the aimer point 134, as the insertion guide 140 is disposed toward the aimer point 134. This allows marking and fixing, via the edge at the tip 141 of the insertion guide 140, an optimal insertion point 172. The optimal insertion point 172 lies on the insertion axis where the insertion guide 140 meets bone, and the edge of the tip 141 allows fixing the insertion guide 140 against the bone for guidewire 154 insertion. The hinge axis 122 and the insertion axis 142 therefore define a placement point 170 representative of an optimal insertion point on the insertion axis 142 for surgical entry, in which the aimer point 134 of the arm disposed at the placement point 172 (target location), as depicted at step 211.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical aiming device comprising:
   a handle coupled to a proximate end of an elongated arm, the elongated arm further having a distal end;
   a hinge securing an aimer to the distal end for rotational communication around a hinge axis, the aimer extending parallel to the hinge axis, the hinge axis and an insertion axis intersecting for defining a placement point representative of an optimal insertion point along the insertion axis for surgical entry;
   the aimer having an elongated aimer tip extending linearly from the hinge along the hinge axis, and an aimer point, the aimer point at a distal end of the aimer tip from the hinge, the aimer tip coupled to the arm via the hinge at a proximate end, and the aimer point of the arm disposed at the placement point, the elongated arm having an arced section and a straight section, the hinge securing the aimer to the straight section distal from the arced section, the aimer point defined by a center of a circle defining the arc in the arced section; and
   the hinge adapted to secure the aimer at a degree of rotation about the axis defined by the hinge rotation, the axis passing through the aimer point, the optimal insertion point being on the insertion axis where the insertion axis intersects extractable material, the hinge axis intersecting the insertion axis for rotational positioning.

2. The device of claim 1 further comprising:
   an aperture in the handle; and
   an insertion guide slideably movable through the aperture in the handle, the aperture defined by the insertion axis extending toward the aimer point.

3. The device of claim 1 wherein the hinge axis is defined by a securing screw, the rotational communication being about an axis defined by the securing screw, the degree of rotation fixable by the securing screw.

4. The device of claim 1 wherein the handle has a slot corresponding to the arced section, the arced section slideably engaging with the slot in the handle for arcuate movement relative to the aimer point.

5. The device of claim 4 further comprising:
   an aperture in the handle; and
   an insertion guide slideably movable through the aperture in the handle, the aperture defined by the insertion axis extending through the aimer point.

6. The device of claim 5 wherein the slot frictionally secures the arced section in the slot for fixing the aimer tip relative to the insertion guide.

7. The device of claim 6 wherein the insertion guide has an engaging edge at a tip and is disposable along the insertion axis toward the optimal insertion point, the optimal insertion point responsive to drilling from the engaging edge of the insertion guide.

8. The device of claim 1 wherein the insertion axis and hinge axis intersect with the aimer point along both the range of arm travel along the arc and range of arm pivot around the hinge axis, the aimer point defining a center of a circle defined by the intersection of the insertion axis and the hinge axis, the radius of the circle remaining fixed during arm pivot and arc travel.

9. The aiming device of claim 1 wherein the aimer point is configured for locating an anatomically sound location on a femur of a patient for a surgical bone tunnel.

10. The aiming device of claim 9 wherein the bone tunnel is defined by the insertion axis and configured for inserting a surgical guidewire therethrough.

11. A surgical aiming device comprising:
a handle having a slot defining an arc;
an arm having an arced section and a straight section, the arced section slideably engaging with the slot in the handle;
a hinge securing an aimer to the straight section distal from the arced section for rotational communication with the straight section around a hinge axis; the aimer extending parallel to the hinge axis;
the aimer having an elongated aimer tip extending linearly from the hinge along the hinge axis and an aimer point, the aimer point at a distal end of the aimer tip from the hinge, the aimer tip coupled to the straight section via the hinge at a proximate end, the hinge securing the aimer to the straight section distal from the arced section, the aimer point defined by a center of a circle defining the arc in the arced section and the arc in the handle through which the arced section slideably engages;
the hinge adapted to secure the aimer at a degree of rotation, the degree of rotation being about the hinge axis defined by the hinge and passing through the aimer point; and
the hinge axis and an insertion axis intersecting for defining a placement point representative of an optimal insertion point along the insertion axis for surgical entry, the aimer point of the arm disposed at the placement point;
the optimal insertion point being on the insertion axis where the insertion axis intersects extractable material, the hinge axis intersection the insertion axis for rotational positioning.

12. The device of claim 1 wherein the hinge axis passes through the aimer point throughout a range of motion of the arced section through the slot.

13. The device of claim 12 further including an insertion guide slideably movable through an aperture in the handle, the aperture defining an insertion axis extending toward center of circle defined by the arc.

14. The device of claim 13 where the aperture axis passes through the aimer point, the insertion guide adapted for rotation around the insertion axis as the insertion guide is disposed toward the aimer point.

15. The device of claim 14 wherein the hinge axis is defined by a securing screw, the rotational communication being about an axis defined by the securing screw, the degree of rotation fixable by the securing screw.

16. The aiming device of claim 11 wherein the arc is coplanar with the aimer point.

17. The aiming device of claim 11 wherein the insertion axis is coplanar with the arc defined by the slideable engagement of the arced section into the handle.

18. A method for surgical drilling, comprising:
engaging a handle having a slot defining an arc in a surgical field for defining a drilling hole;
disposing an arm having an arced section and a straight section, the arced section slideably engaging with the slot in the handle for arcuate movement therein;
pivoting a hinge securing an aimer to the straight section distal from the arced section for rotational communication with the straight section around a hinge axis, the aimer extending parallel to the hinge axis;
the aimer having an elongated aimer tip extending linearly from the hinge along the hinge axis and an aimer point, the aimer point at a distal end of the aimer tip from the hinge, the aimer tip coupled to the straight section via the hinge at a proximate end, the hinge securing the aimer to the straight section distal from the arced section, the aimer point defined by a center of a circle defining the arc in the arced section and the arc in the handle through which the arced section slideably engages;
the pivoting disposing the aimer tip at a placement point along an axis defining an insertion path;
the hinge adapted to secure the aimer at a degree of rotation, the degree of rotation being about the axis defined by the hinge and passing through the aimer point, the hinge axis and an insertion axis intersecting for defining a placement point representative of an optimal insertion point along the insertion axis for surgical entry, the aimer point of the arm disposed at the placement point; and
the optimal insertion point being on the insertion axis where the insertion axis intersects extractable material, the hinge axis intersecting the insertion axis for rotational positioning.

19. The method of claim 18 wherein the hinge axis passes through the aimer point throughout a range of motion of the arced section through the slot.

20. The method of claim 19 further including:
disposing an insertion guide, the insertion guide slideably movable through an aperture in the handle, the aperture defining an insertion axis extending toward the center of a circle defined by the arc.

21. The method of claim 20, the disposing further comprising, wherein the aperture axis passes through the aimer point, advancing the insertion guide along the insertion axis as the insertion guide is disposed toward the aimer point.

22. The method of claim 21 further comprising marking, via an engaging edge in the insertion guide, an optimal insertion point, wherein the hinge axis and the insertion axis define a placement point representative of an optimal insertion point on the insertion axis for surgical entry, the aimer point of the arm disposed at the placement point.

23. The method of claim 22 wherein the hinge axis is defined by a securing mechanism, the rotational communication being about an axis defined by the securing mechanism, the degree of rotation fixable by the securing mechanism.

24. A surgical aiming device comprising:
a handle having an insertion guide defining an insertion axis and an arced slot defining a circle having a center;
an arm having an arced section and a straight section, the arced slot adapted to receive the arced section and the straight section having a hinge defining a hinge axis;
an elongated aimer attached at the hinge and adapted for rotation around the hinge axis, the elongated aimer extending parallel to the hinge axis and having an aimer point at a distal end, the elongated aimer attached to the hinge at a proximate end and extending linearly along the hinge axis to the aimer point;
the insertion axis responsive to slideable engagement of the arced section with the straight section;
the arm responsive to pivoting around the elongated aimer on the hinge axis;
the insertion axis and the hinge axis intersecting at the center of the defined circle during the slideable engagement and the pivoting around the hinge axis, the insertion guide aligned with the insertion axis for receiving a surgical instrument adapted to exit from a surgical tunnel at a location defined by the aimer point.

25. The device of claim 24 wherein the elongated aimer is adapted for insertion between a tibia and femur of a surgical patient for engaging an exit location on the tibia or femur.

* * * * *